United States Patent [19]

Harris et al.

[11] 4,432,988
[45] Feb. 21, 1984

[54] ANTI-THROMBOTIC DIAZABICYCLOÖCTANEDIONES

[75] Inventors: Clifford J. Harris, Orpington; Paul Barraclough, Maidstone, both of England

[73] Assignee: The Wellcome Foundation Ltd., United Kingdom

[21] Appl. No.: 296,138

[22] Filed: Aug. 25, 1981

[30] Foreign Application Priority Data

Aug. 26, 1980 [GB] United Kingdom ............... 8027561

[51] Int. Cl.$^3$ .................. A61K 31/415; C07D 235/02
[52] U.S. Cl. ............................. 424/273 R; 542/413; 542/426; 548/253; 548/302
[58] Field of Search ............... 548/302, 253; 542/413, 542/426; 424/273 R

[56] References Cited

PUBLICATIONS

*Chemical Abstracts*, 91:175344w (1979).
*Chemical Abstracts*, 94:103365t (1981).

*Primary Examiner*—Richard A. Schwartz
*Attorney, Agent, or Firm*—Donald Brown

[57] ABSTRACT

Compounds of the general formula

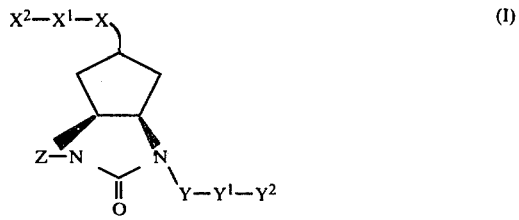

[wherein
X represents a sulphur atom (—S—) or oxygen atom (—O—) in the $\alpha$ or $\beta$-configuration;
$X^1$ represents a $C_{1-5}$ straight chain or branched alkylene group or $C_{3-5}$ straight chain or branched alkenylene group;
$X^2$ represents a carboxyl, carboxamide, hydroxymethlene, alkoxycarbonyl or 5-tetrazolyl group;
Z represents a hydrogen atom or a $C_{1-4}$ straight chain or branched alkyl group;
Y represents a group of formula —$CR_2$-$CH_2$— in which each R is independently selected from hydrogen and methyl;
$Y^1$ represents a methylene group substituted by hydroxyl, a methylene group substituted by hydroxyl and alkyl, a methylene group or carbonyl group, and
$Y^2$ represents a $C_{1-7}$ straight chain or branched alkyl group, phenyl, benzyl or a $C_{4-7}$ cycloalkyl group] and salts of those compounds of formula (I) wherein $X^2$ represents a carboxyl group and/or wherein Z represents a hydrogen atom.

These compounds have anti-aggregatory effect on blood platelets and are useful in the treatment or prophylaxis of thrombo-embolic disorders. Processes for the preparation of the compounds are described.

12 Claims, No Drawings

ANTI-THROMBOTIC DIAZABICYCLODCTANEDIONES

This invention relates to novel diazabicycloctanedione derivatives.

2,4-Diazabicyclo[3.3.0]octane-3,7-dione derivatives, defined below in formula (I), have been found to have pharmacological properties related to those of natural prostaglandins, as demonstrated by their ability to mimic or antagonise the physiological effects of the natural prostaglandins in various biological preparations.

Thus, according to one feature of the present invention we provide compounds of the general formula

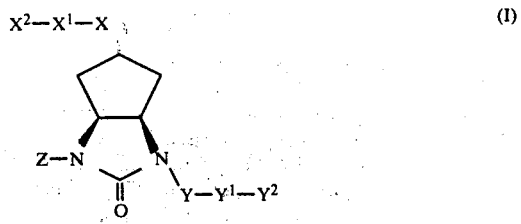

X represents a sulphur atom (—S—) or oxygen atom (—O—) in the α- or β-configuration;

$X^1$ represents a $C_{1-5}$ straight chain or branched alkylene group or $C_{3-5}$ straight chain or branched alkenylene group;

$X^2$ represents a carboxyl, carboxamide, hydroxymethylene, alkoxycarbonyl or 5-tetrazolyl group;

Z represents a hydrogen atom or a $C_{1-4}$ straight chain or branched alkyl group;

Y represents a group of formula —$CR_2$—$CH_2$— in which each R is independently selected from hydrogen and methyl;

$Y^1$ represents a methylene group substituted by hydroxyl, a methylene group substituted by hydroxyl and alkyl, a methylene group or a carbonyl group, and $Y^2$ represents a $C_{1-7}$ straight chain or branched alkyl group, phenyl, benzyl or a $C_{4-7}$ cycloalkyl group. Included in the meaning of the compounds of formula (I) are the salts of those compounds in formula (I) wherein $X^2$ represents a carboxyl group and also the salts which may be formed when Z is hydrogen.

Preferred compounds of formula (I) include those wherein X represents a sulphur atom, for example in the β-configuration, and $X^2$ represents a carboxyl group. $X^1$ advantageously represents a straight chain propylene group. Z is preferably a hydrogen atom. In the 2-position side chain Y is preferably a —$CH_2$—$CH_2$— group and $Y^1$ is preferably a methylene group substituted by hydroxyl (the hydroxyl substituted preferably being in the β-configuration). $Y^2$ is preferably a $C_{4-6}$ straight chain or branched alkyl group (particularly a pentyl group) or a cyclohexyl group.

In the alkoxycarbonyl group represented by $X^2$ in formula (I), the alkyl moiety may contain 1 to 6 carbon atoms, methyl and ethyl groups being preferred. Such groups are also preferred as substituents of the methylene group represented by $Y^1$ in formula (I).

Particularly valuable salts for medical purpose are those having a pharmaceutically acceptable cation such as an alkali metal e.g. sodium and potassium, an alkaline earth metal e.g. calcium and magnesium, ammonium or an organic base, particularly an amine such as ethanolamine. Salts having non-pharmaceutically acceptable cations are included within the ambit of this invention as useful intermediates for the production of pharmaceutically acceptable salts, and of the acids or esters of formula (I).

Except when there is clear indication to the contrary, formula (I) and other formulae in the specification embrace all stereoisomers represented therein. In particular such formulae include the enantiomeric forms, racemates and diastereomers. Thus, for example, the compounds of formula (I) contain an additional asymmetric carbon atom when $Y^1$ includes a hydroxyl group. The diastereomers arising from this additional asymmetric carbon atom may be separated in conventional manner, e.g. by column chromatography.

The compounds of formula (I) are of value in having pharmacological properties related to those of natural prostaglandins; thus, the compounds may mimic or antagonise the biological effects of members of the prostaglandin (PG) 'A', 'B', 'C', 'D', 'E' and 'F' series. For example, compounds of formula (I) have been found to mimic the anti-aggregatory effect of $PGE_1$ on blood platelets.

By reason of their prostaglandin-related properties, the compounds of formula (I) are useful in the pharmacological characterisation and differentiation of the biological activities of the natural prostaglandins and their 'receptors'. The further understanding of the physiological role of prostaglandins is of course valuble in the search for new and improved therapeutic substances.

The compounds of formula (I) are also of value as therapeutic agents. The present invention therefore provides the above-defined compounds of formula (I) and their salts for use in a method of treatment of the human or animal body by therapy, particularly the treatment or prophylaxis of a thrombo-embolic disorder in a human or animal body. It is to be understood that the term "thrombo-embolic disorder" includes those disorders whose etiology is associated with platelet aggregation.

In particular compounds of formula (I) such as the preferred classes of compounds described above and especially 1β, 5β, 7α-2-(3-cyclohexyl-3β-hydroxypropyl)-7-(3-carboxypropylthio)-2,4-diazabicyclo[3.3.0]octan-3-one, of formula

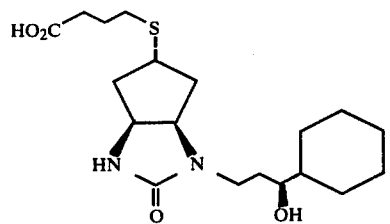

have a potent anti-aggregatory effect on blood platelets and are useful whenever it is desired to inhibit platelet aggregation or to reduce the adhesive character of platelets, for example in the treatment or prevention of the formation of thrombi in mammals, including man. The compounds are particularly useful in the treatment and prevention of myocardial infarcts, thromboses, and strokes. The compounds may also be used to promote patency of vascular grafts following surgery, and to treat complications of arteriosclerosis and conditions such as atherosclerosis, blood clotting defects due to lipidemia, and other clinical conditions in which the underlying aetiology is associated with lipid imbalance or hyperlipidemia. A further use for such compounds is as an additive to blood and other fluids which are used in artificial extracorporeal circulation and perfusion of isolated body portions. The compounds of formula (I) may also be used in the treatment of peripheral vascular disease and angina.

In experiments which have been carried out on the rat, compounds of formula (I) have been shown to have a very low ore negligible hypotensive effect which may be of advantage in clinical situations where a hypotensive or vasodilatory effect is undesirable.

Those compounds of formula (I) which mimic the effect of $PGE_1$ of antagonising histamine-induced bronchoconstriction may be used in the treatment or prophylaxis of bronchial asthma and bronchitis by alleviating the bronchoconstriction associated with this condition.

Compounds of formula (I) such as $1\beta$, $5\beta$, $7\alpha$-(3-carboxypropylthio)-2-(3-hydroxyoctyl)-2,4-diazabicyclo[3.3.0]-octan-3-one and $1\beta$, $5\beta$, $7\alpha$-3-(cyclohexyl-3-hydroxypropyl)-7-(3-carboxypropylthio)-2,4-diazabicyclo/3.3.0/-octan-3-one, which inhibit pentagastrin-induced gastric acid secretion and reduce the formation of indomethacin-induced gastric lesions in rats are useful in reducing excessive gastric secretion, reducing and avoiding gastro-intestinal ulcer formation and accelerating the healing of such ulcers already present in the gastrointestinal tract whether such ulcers arise spontaneously or as a component of polyglandular adenoma syndromes.

In addition the compounds of formula (I) may be used in the treatment of proliferative skin diseases such as are associated with excessive cell division in the epidermis or dermis which may be accompanied by incomplete cell differentiation. Particular conditions which may be alleviated include psoriasis, atopic dermatitis, nonspecific dermatitis, primary irritant contact dermatitis, allergic contact dermatitis, basal and squamous cell carcinomas of the skin, lamellar icthyosis, epidermolytic hyperkeratosis, premalignant sun-induced keratosis, non-malignant keratosis, acne, and seborrheic dermatitis in humans and atopic dermatitis and mange in domestic animals. For the treatment of these conditions the compounds are desirably applied topically to the affected skin. Alternatively they may be administered by an intradermal or intramuscular injection, for example directly into the skin lesion or into the surrounding tissue. Injectable compositions will generally contain from 0.1 to 0.5% w/v of active ingredient.

A further use for compounds of formula (I) which mimic the uterine smooth muscle effects of $PGE_2$ and $PGF_{2\alpha}$ is as anti-fertility agents, in particular as abortifacients.

The amount of a compound of formula (I) required to achieve the desired biological effect will of course depend on a number of factors, for example, the specific compound chosen, the use for which it is intended, the mode of administration, and the recipient. In general, a daily dose may be expected to lie in the range of from 1 $\mu$g to 20 mg per kilogram bodyweight. For example, an intravenous dose may lie in the range of from 5 $\mu$g to 1 mg/kg which may conveniently be administered as an infusion of from 0.01 to 50 $\mu$g per kilogram per minute. Infusion fluids suitable for this purpose may contain from 0.001 to 100, for example from 0.01 to 10 $\mu$g per milliliter, preferably 1 to 10 $\mu$g/ml. Unit doses may contain from 10 $\mu$g to 100 mg of a compound of formula (I), for example, ampoules for injection may contain from 0.01 to 1 mg, and orally administrable unit dose formulations such as tablets or capsules may contain from 0.1 to 50, for example 2 to 20 mg. Such dosage units may be administered for example, 1,2,3 or 4 times per day, separately or in multiples thereof.

More specifically, when a compound of formula (I) is used to inhibit platelet aggregation it is generally desirable to achieve a concentration in the appropriate liquid, whether it be the blood of a patient or a perfusion fluid, of about 1 $\mu$g to 10 mg, for example from 10 $\mu$g to 1 mg, per liter.

The abovementioned doses refer to the acids, amides, ester and alcohols of formula (I); where a salt is used, the dose should be taken as referring to the corresponding anion.

According to a further feature of the present invention we provide pharmaceutical formulations comprising, as active ingredient, at least one compound of formula (I) and/or a pharmacologically acceptable salt thereof (as defined above) together with at least one pharmaceutical carrier or excipient. These pharmaceutical formulations may be used in the treatment or prophylaxis of the conditions referred to above. The carrier must of course be 'acceptable' in the sense of being compatible with the other ingredients of the formulation and not deleterious to the recipient thereof. The carrier may be a solid or a liquid, and is preferably formulated with a compound of formula (I) as a unit-dose formulation, for example a tablet, which may contain from 0.05% to 95% by weight of the active ingredient. Other pharmacologically active substances may also be present in formulations of the present invention for example $\beta$-adrenoceptor blocking agent such as propranolol. The compound of formula (I) may be incorporated in the formulations either in the form of an acid or a salt or ester thereof, and the formulations may be prepared by any of the well-known techniques of pharmacy consisting essentially of admixture of the components of the formulation.

The formulations include those suitable for oral, rectal, topical, (e.g. buccal such as sub-lingual) or parenteral (e.g. subcutaneous, intramuscular or intravenous) administration, although the most suitable route in any given case will depend in the nature and severity of the condition being treated, and on the nature of the active compound.

Formulations suitable for oral administration may be presented as discrete units such as capsules, cachets, lozenges or tablets each containing a predetermined amount of the active compound; as powders or granules; as solutions or suspensions in aqueous non-aqueous liquids; as oil-in-water emulsions; or as water-in-oil liquid emulsions,. Such formulations may be prepared by any of the methods of pharmacy but all methods include the step of bringing into association the active ingredient with the carrier which comprises one or more appropriate ingredients. In general, the formulation may be prepared by uniformly and intimately admixing the active ingredient with liquids or finely divided solid carriers or both, and then, if necessary, shaping the product into the desired presentation. For example a tablet may be prepared by compression or moulding a powder or granules of the active ingredient, optionally with one or more accessory ingredients. Compressed tablets may be prepared by compressing, in a suitable machine, the active ingredient in a free-flowing form such as a powder or granules optionally mixed with a binder, lubricant, inert diluent, surface active or dispersing agent(s). Moulded tablets may be made by moulding in a suitable machine the powdered active ingredient moistened with an inert liquid diluent.

Formulations suitable for buccal (e.g. sub-lingual) administration include lozenges comprising the active ingredient compound in a flavoured bases, e.g. sucrose and acacia or tragacanth; and pastilles comprising the active ingredient in an inert base such as gelatin and glycerin; or sucrose and acacia.

Formulations of the present invention suitable for parenteral administration conveniently comprise sterile aqueous preparations of the active ingredient which preparations are preferably isotonic with the blood of the intended recipient. These preparations are preferably administered intravenously, although administration may also be effected by means of subcutaneous or intrasmucular injection. Such preparations may be conveniently prepared by admixing the active ingredient with water and rendering the product sterile and isotonic with the blood.

Formulations suitable for rectal administration are preferably presented as unit-dose suppositories. These may be prepared by admixture of the active ingredient with one or more conventional solid carriers, forming the suppository base for example cocoa butter, and shaping of the resulting mixture.

Formulations suitable for topical application to the skin preferably take the form of an ointment, cream, lotion, paste, gel, spray, aerosol or oil. Carriers which may be used in such formulations include petroleum jelly, lanolin, polyethylene glycols, alcohols and combinations thereof. The active ingredient is generally present in a concentration of from 0.1 to 15% w/w of the composition, for example from about 0.5 to about 2%.

According to a still further feature of the present invention we provide a process for the preparation of compounds of formula (I) and salts thereof which comprise reacting a compound of formula $$X^2-X^1-X-H \qquad (II)$$

(wherein X, $X^1$, and $X^2$ are as hereinbefore defined) or a functional equivalent thereof with a compound of formula

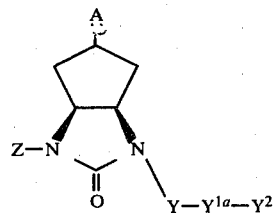

(III)

(wherein Z, Y and $Y^2$ are as defined above and $Y^{1a}$ has the meanings given above for $Y^1$ with the additional possibilities that it may also represent a methylene group substituted by a protected hydroxy group or by an alkyl group and a protected hydroxy group and A represents a leaving group in the α- or β-configuration which is displaceable by the compound of formula (II) e.g. a hydrocarbon sulphonyloxy group, such as a p-toluenesulphonyloxy or methanesulphonyloxy group, or a halogen atom such as a chlorine atom) and subsequently if desired, removing any hydroxy protecting group which may be present.

The compound of formula (II) may be conveniently employed in the form of a salt, for example of formula $$X^2-X^1-X^--M^+$$

where $M^+$ is an alkali metal, e.g. sodium cation. The salt may be prepared by treatment of a compound of formula (II) with an alkali metal alkoxide such as sodium methoxide. The salt may alternatively be prepared from the corresponding lactone particularly when the group $X^1$ represents a $C_{3-4}$ alkylene group.

The reaction of the compound of formula (II) or a functional equivalent thereof with the compound of formula (III) is advantageously effected in a polar organic solvent medium, e.g. dimethylsulphoxide or an amide solvent such as dimethylformamide, conveniently at ambient temperature.

When using the above process to prepare a compound of formula (I) in which the group X is in the α-configuration a compound of formula (II) in which the leaving group A is in the β-configuration should be used. Similarly, with a compound of formula (I) in which X is in the β-configuration, a starting material of formula (III) in which the leaving group A is in the β-configuration will be required. The latter starting materials may be prepared from a corresponding starting material of formula (III) containing a different leaving group in the β-configuration by reacting the latter material with a suitable reagent serving to replace the first leaving group (in the β-configuration) with a second (desired) leaving group (in the α-configuration). Thus, for example, a compound of formula (III) in which A represents a halogen atom in the β-configuration may be prepared by reaction of a corresponding compound of formula (III) in which A represents a hydrocarbon sulphonyloxy group in the β-configuration with an appropriate source of halide anions e.g. an alkali metal halide such as lithium chloride.

The compounds of formula (III) wherein A represents a leaving group in the β-configuration may be prepared for example by reacting a compound of formula

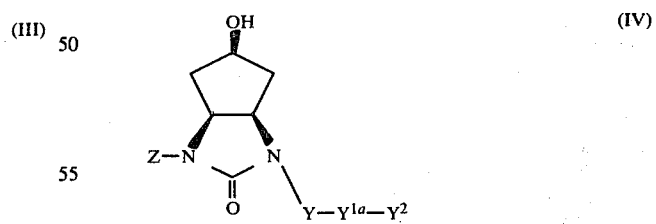

(IV)

(wherein Z, Y, $Y^{1a}$ and $Y^2$ are as hereinbefore defined) with an appropriate reagent serving to introduce the group A in the β-configuration. Thus, for example, a compound of formula (IV) may be reacted with a hydrocarbon sulphonyl halide (e.g. chloride) to introduce a hydrocarbon sulphonyl group. The reaction is conveniently effected in the presence of an organic base such as pyridine.

The compounds of formula (IV) may be prepared for example by reacting a compound of formula

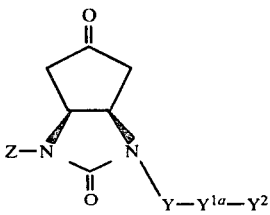

(V)

(wherein Z, Y, $Y^{1a}$ and $Y^2$ are as hereinbefore defined) with an appropriate reducing agent for example a metal borohydride or substituted borohydride, particularly sodium borohydride.

The present invention provides compounds of the general formula

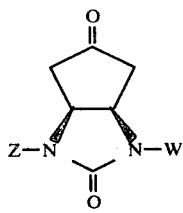

(VA)

wherein Z is as hereinbefore defined and W represents a hydrogen atom or a group of formula

$Y-Y^{1a}-Y^{2a}-Y^{3a}$ wherein Y and $Y^{1a}$ are as hereinbefore defined, $Y^{2a}$ represents a covalent bond or straight or branched alkylene group having 1 to 7 carbon atoms optionally substituted in the carbon adjacent $Y^{1a}$ by one or two groups each of which may be alkyl or a cyclic radical; $Y^{3a}$ represents hydrogen, hydroxy, alkoxy of 1 to 7, preferably 1 to 4, carbon atoms, a cyclic radical, phenyl, benzyl, phenoxy or benzyloxy, wherein each of phenyl, benzyl, phenoxy and benzyloxy may be substituted in the benzene ring by one or more groups selected from hydroxy, halogeno, nitro, amino, acylamino, alkenyl, alkoxy, phenyl and alkyl which may itself be substituted by one or more halogeno groups; or $Y^{2a}$ and $Y^{3a}$ together form an alkyl group of 1 to 7 carbon atoms having at least one hydrogen replaced by fluoro; or Y is a bond, —$CH_2$— or —$CH_2.CH_2$— and $Y^{1a}$, $Y^{2a}$ and $Y^{3a}$ taken together form a cycloalkyl or bicycloalkyl group substituted by a hydroxyl group which preferably has three carbon atoms separating it from the hydantoin ring.

In the definitions of $Y^{2a}$ and $Y^{3a}$ in formula (Va) the term cyclic radical means the monovalent radical derived by loss of a ring hydrogen atom from a monocyclic or polycyclic compound having from 3 to 12 ring atoms selected from carbon, nitrogen, oxygen and sulphur, which compound may be saturated or unsaturated and may be further substituted by one or more alkyl groups, but excluding phenyl. Such cyclic radicals include cycloalkyl radicals having 3 to 10 carbon atoms such as cyclopropyl, cyclopentyl, cyclohexyl and cyclooctyl, bicycloalkyl radicals having 4 to 10 carbon atoms such as adamantyl or norbornanyl (bicyclo[2,2,1-]heptyl), spiroalkanyl radicals having 5 to 12 carbon atoms such as 2-spiro[3,3]heptyl, 1-spiro[4,4]nonane and 8-spiro[4,5]decane, cycloalkenyl radicals having 4 to 10 carbon atoms such as 4-cyclopentene, heterocyclic radicals such as tetrahydrofuranyl and tetrahydropyranyl and heteroaryl radicals such as thienyl, furyl, pyridyl, pyrimidyl, thiazolyl, imidazolyl and diazepinyl. Included in the term cyclic radical are these wherein one or more hydrogen atoms are replaced by fluoro.

The compounds of formula (VA) are useful as intermediates or starting materials for the preparation of a wide variety of prostaglandin analogues and other compounds of related structure. Among the prostaglandin analogues which may be prepared from the compounds of formula (VA) are compounds of formula

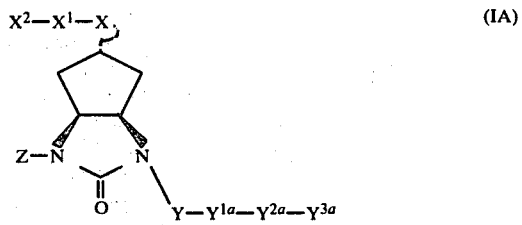

(IA)

(wherein X, $X^1$, $X^2$, Y, $Y^{1a}$, $Y^{2a}$, $Y^{3a}$, and Z are as hereinbefore defined), such compounds including the particular class of compounds represented by formula (I) above. These compounds of formula (IA) comprise compounds which generally have the broad profile of pharmacological properties described above for the compound of formula (I) and which may be prepared in an analogous manner to the latter compounds.

The compounds of formula (VA) may be prepared from compounds of formula

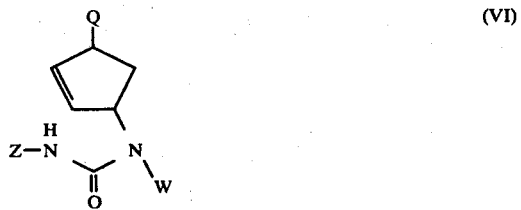

(VI)

(wherein W and Z are as hereinbefore defined and Q represents a ketone protecting group, e.g. an ethylenedioxy group) by cyclisation under aqueous acidic conditions, for example, using a strong acid. This reaction conveniently results in the deprotection of the ketone group in the cyclopentane ring and the concomitant cyclisation of the heterocyclic ring. The reaction may be effected, if desired, in the presence of an inert solvent for example a hydrocarbon solvent such as petrol or more preferably an ether solvent such as tetrahydrofuran.

Compounds of formula (IV) may be prepared for example by reaction of a compound of formula

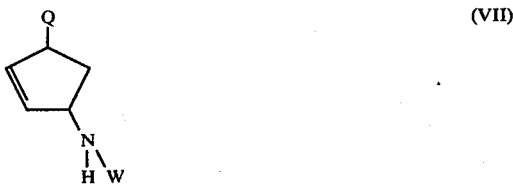

(VII)

(wherein Q and W are as defined above) with cyanic acid or an alkyl isocyanate depending respectively on whether Z in formula (VA) is hydrogen or alkyl.

When cyanic acid is used, it is conveniently produced in situ by the use of an alkali metal cyanate, e.g. potassium cyanate, and an acid, e.g. an equivalent amount of mineral acid which may be added to the reaction medium; desirably an inert solvent is present which is preferably polar such as water or a mixture of water with acetone, dimethylformamide, dimethylsulphoxide or a lower alkanol such as ethanol. Alternatively the solvent may be a hydrocarbon, an ether or halogenated hydrocarbon such as chloroform. Where desired, the reaction may be promoted by heating the reactants.

Similar reaction conditions may be used when an alkyl isocyanate is used except that it is unnecessary to provide an equivalent amount of acid, as an acid addition salt or otherwise, in the reactants.

Instead of using a cyanate or isocyanate, a compound of formula (VII) may be reacted with for example, urethane, urea, nitrourea or an N-alkylurea. A solvent is not essential but if desired an inert solvent may be used such as one mentioned above for the reaction of the compound of formula (VII) with cyanic acid. The reaction is preferably effected at an elevated temperature, for example from 100° to 125° C. but temperatures of up to 150° C. may be employed.

In the above described synthesis, the intermediate of formula (VI) need not be isolated from the reaction mixture and may be converted directly to compounds of formula (VA) under the described reaction conditions.

Compounds of formula (VII) wherein W represents a group of formula $-Y-Y^{1a}-Y^{2a}-Y^{3a}$ (wherein Y, $Y^{1a}$, $Y^{2a}$ and $Y^{3a}$ are as hereinbefore defined) may be prepared for example by reacting a compound of formula (VIII) with a compound of formula (IX):

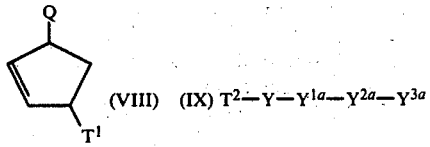

(wherein Q, Y, $Y^{1a}$, $Y^{2a}$ and $Y^{3a}$ are as hereinbefore defined, one of $T^1$ and $T^2$ is amino and the other is halo (preferably bromo) or sulphonyloxy. The reaction is preferably effected in a solvent medium, e.g. a hydrocarbon solvent such as toluene.

The intermediates of formula (VII) wherein W is $-Y-Y^{1a}-Y^{2a}-Y^{3a}$ when $Y^{1a}$ is carbonyl may also be prepared by reaction of an amine of formula (VIII) wherein $T^1$ is amino with an unsaturated ketone of formula

$$CR_2=CH.CO.Y^{2a}.Y^{3a} \qquad (X)$$

wherein $Y^{2a}$ and $Y^{3a}$ have the same meaning as in formula (VII) and R is as defined in the definition of Y in formula (I); the reaction being effected in the presence or absence of an inert solvent, and at room temperature or optionally with heating.

Compounds of formula (VIII) may be prepared from cyclopent-2-enone in conventional manner, for example according to the method of DePuy (J. Org. Chem., 1964, 29, 3508) in the case of the preparation of 5-bromo-3,3-ethylenedioxycyclopentene. Compounds of formula (VIII) wherein $T^1$ is amino may be prepared from compounds of formula (VIII) wherein $T^1$ is halo, e.g. bromo, by reaction with sodium azide and subsequent catalytic reduction.

The present invention also provides an alternative process for the preparation of compounds of formula (I) and the above-identified salts which comprises reacting a compound of formula

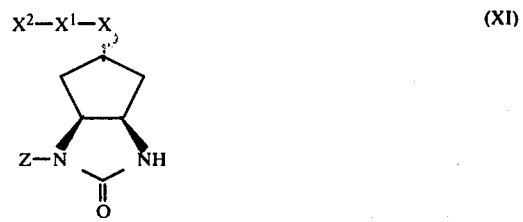

(wherein X, $X^1$, $X^2$ and Z are as defined above) with a compound of formula

$$Hal-Y-Y^{1a}-Y^2 \qquad (XII)$$

(wherein Y, $Y^{1a}$ and $Y^2$ are as hereinbefore defined and Hal is a halo radical preferably bromo) and subsequently, if desired, removing any hydroxy protecting group which may be present. The reaction may be effected by formation of a salt of a compound of formula (XI), e.g. by treatment with sodium hydride in an inert solvent and subsequent reaction with the compound of formula (XII).

The compounds of formula (I) wherein $Y^{1a}$ is carbonyl may alternatively be prepared by reaction of a compound of formula (XI) with a compound of formula (X) as defined above.

The compound of formula (XI) employed as starting material in the above-described process may be prepared from a compound of formula (VII) wherein W represents a hydrogen atom using the same general procedures previously described for the preparation of compounds of formula (I), (III) and (IV)

Compounds of formula (VA) wherein Z and W both represent hydrogen atoms are useful as intermediates in the preparation of analogues of biotin.

In the preparation of compounds of formula (I) and intermediates therefor, it may be desirable to protect any labile hydroxy group present in the molecule by the use of an appropriate protecting group. Such protecting groups are well-known in the art and include acyl (e.g. $C_{1-6}$ alkanoyl such as acetyl or aroyl), tetrahydropyran-2-yl, 1-ethoxyethyl, aralkyl such as benzyl, and silyl (e.g. trialkylsilyl such as trimethylsilyl).

Removal of protecting groups may be carried out by appropriate methods known to those skilled in the art. For example, an acyl group may be removed by acid or base hydrolysis and a benzyl group by reductive cleavage, e.g. by hydrogenolysis using for example a palladium/charcoal catalyst.

In the preparation of compounds of formula (I) the hydroxy group present in the hydroxymethylene group which may be represented by $Y^{1a}$ in formulae (III), (IV) and (V) is preferably protected using an acetyl protecting group, which may be conveniently introduced by reacting an appropriate compound of formula (V) with an acetylating agent such as acetic anhydride. The acetyl protecting group may be removed, for example, after reaction of the compounds of formula (II) and (III), e.g. by base hydrolysis.

Another instance where protection of a hydroxy group may be desirable is in the reaction of a compound of formula (VIII) with a compound of formula (IX) where any hydroxy group in $Y^{1a}$ of the latter compound is desirably protected, for example by an aralkyl group such as a benzyl group. This protecting group may be subsequently removed at a later convenient stage in the synthesis, for example, after the cyclisation of the compound of formula (VI) to form a compound of formula (VA).

It will be appreciated that a compound of formula (I) wherein $Y^1$ is carbonyl may be converted to the corresponding secondary alcohol by reduction with a suitable reducing agent, such as sodium borohydride. Also, an alcohol of formula (I) wherein $Y^1$ is —CH.OH— may be oxidised to the corresponding ketone using Jones' reagent, acid dichromate or any other suitable reagent.

The alcohols of formula (I) wherein $X^2$ is hydroxymethylene may also be obtained by reduction with an appropriate reducing agent of the corresponding acid, ester, acid halide, acid anhydride or aldehyde. The appropriate reducing agent will depend on the particular substrate, but a reactant which may in general be used is lithium borohydride. In particular a carboxylic acid may for example be converted to a corresponding mixed anhydride with ethylchloroformate in the presence of a base such as triethylamine, and subsequently reduced to the alcohol using sodium borohydride. Similarly an ester may be reduced to the alcohol using di-iso-butyl aluminium hydride in an inert solvent such as ether or hydrocarbon such as hexane or benzene. Such alcohols may also be prepared by catalytic hydrogenation.

Alternatively the alcohols of formula (I) wherein $X^2$ is hydroxymethylene may be prepared by hydrolysis of a corresponding halide with an appropriate reagent. For this purpose a hydroxide may be used for example an aqueous alkali or a suspension of silver oxide in water.

The salts of compounds of formula (I) wherein $X^2$ is carboxyl and/or Z is hydrogen may be prepared in conventional manner.

The following Examples illustrate the present invention.

PREPARATION 1

2-cis-, 2-trans-3-Cyclohexylacrylonitrile

A suspension of sodium hydride (100%, 10.93 g) in dry N,N-dimethylformamide (DMF) (230 ml) was stirred vigorously under dry nitrogen and diethyl cyanomethylphosphonate (81,00 g) in dry DMF (65 ml) was added dropwise. After the addition was complete, the mixture was heated at 80° until gas evolution ceased. The solution was cooled and cyclohexanecarboxaldehyde (51.10 g) was added dropwise at 30°. The resulting solution was stirred at room temperature for 1 hr then diluted with water and the product extracted into n-pentane. The combined organic extracts were washed with water, dried (MgSO$_4$), the solvent removed in vacuo, and the residual oil distilled, giving a mixture of 2-cis- and -2-trans-3-cyclohexylacrylonitrile as a colourless oil, b.p. 53°-60°/0.8 mm.

PREPARATION 2

3-Benzyloxy-3-cyclohexylpropylamine

The foregoing mixture of 2-cis and 2-trans-3-cyclohexylacrylonitrile (26.50 g) was dissolved in sodium benzylate solution prepared from sodium (0.65 g) and benzyl alcohol (90 ml) and the resulting solution heated on the steam-bath with stirring for 4 hours then set aside at room temperature for 18 hours. The resulting dark solution was diluted with ether and washed with water. The ethereal extract was dried (Na$_2$SO$_4$), the solvent removed in vacuo, and the residue unchanged nitrile removed by distillation under high vacuum. The residual material was taken up in ether, decolorised with activated charcoal, filtered, and the solvent removed in vacuo. The residual yellow syrup (ca. 22 g) was dissolved in dry ether (40 ml) and added dropwise at +5° to a stirred suspension of lithium aluminium hydride (3.4 g) in dry ether (125 ml). After 1 hour at room temperature, the reaction mixture was treated with water and the resulting gel filtered through Celite. The yellow organic phase was separated, dried (MgSO$_4$), the solvent removed in vacuo, and the residual orange oil distilled, giving 3-benzyloxy-3-cyclohexylpropylamine as a colourless viscous oil, b.p. 120°-5°/0.05-0.06 mm.

EXAMPLE 1

N-(3-Benzyloxyoctyl)-4,4-ethylenedioxycyclopent-2-enamine

5-Bromo-3,3-ethylenedioxycyclopentene was prepared from cyclopent-2-enone (5.0 g) by the method of DePuy (J. Org. Chem., 1964, 29, 3508) and dissolved in dry toluene (50 ml). The solution was added dropwise with stirring to 3-benzyloxyoctan-1-amine (9.48 g) in dry toluene (40 ml) at −25°. The brown solution was stirred for 26 hr at room temperature then at 40° for 3.5 hour then triethylamine (6.0 g) was added. The resulting cloudy solution was washed with three portions of water, then dried (MgSO$_4$) and the solvent evaporated in vacuo giving a red oil. Purification by column chromatography (silica, 100:7 chloroform:methanol) gave the mixture of diastereomers of N-(3-benzyloxyoctyl)-4,4-ethylenedioxycyclopent-2-enamine as a pale red oil, δ (CDCl$_3$) 0.88 (3H, bt, —CH$_3$), 3.92 (4H, s, —O—CH$_2$—CH$_2$—O—), 4.50 (2H, s, —CH$_2$—Ph), 7.31 (5H, bs, —Ph).

EXAMPLE 2

N-(3-Benzyloxy-3-cyclohexylpropyl)-4,4-ethylenedioxycyclopent-2-enamine

The title compound was obtained from 3-benzyloxy-3-cyclohexylpropylamine in an analogous manner to that described in Example 1, δ (CDCl$_3$) 3.90 (4H, s, —O—CH$_2$CH$_2$—O—), 4.53 (2H, s, —CH$_2$Ph), 7.35 (5H, bs, —Ph).

EXAMPLE 3

2-(3-Benzyloxyoctyl)-cis-2,4-diazabicyclo-[3.3.0]octane-3,7-dione

N-(3-Benzyloxyoctyl)-4,4-ethylenedioxycyclopent-2-enamine (972 mg) in ethanol (60 ml) was treated with potassium cyanate (360 mg) in water (4.0 ml) then 1,0 N aqueous hydrochoric acid (3.0 ml) at room temperature. After 18 hours, the mixture was diluted with water and extracted with chloroform. The extract was dried then decolourised and the solvent was removed in vacuo to give crude N-(3-benzyloxyoctyl)-N-(4,4-ethylenedioxycyclopent-2-enyl)urea as a yellow glass. This material was dissolved in tetrahydrofuran (11.0 ml) and 2.0 N aqueous hydrochloric acid (11.0 ml) and the solution set aside at room temperature for 1.25 hours. After dilution with water, the product was extracted into chloroform, and the solvent removed from the dried extract to give the mixture of diastereomers of 2-(3-benzyloxyoctyl)-cis-2,4-diazabicyclo[3.3.0]octane-3,7-dione as a colourless glass, δ (CDCl₃) 0.95 (3H, bt, —CH₃), 2.41

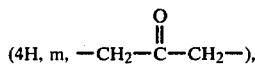
(4H, m, —CH₂—C—CH₂—), 3.40 (2H, m, —N—CH₂—), 4.24 (2H, m, 1-H, 5-H), 4.48 and 4.50 (total 2H, both s, —CH₂Ph from each isomer), 7.31 (5H, bs, —Ph).

EXAMPLE 4

2-(3-Benzyloxy-3-cyclohexylpropyl)-cis-2,4-diazabicyclo[3.3.0]octane-3,7-dione

The title compound was prepared from N-(3-benzyloxy-3-cyclohexylpropyl)-4,4-ethylenedioxycyclopent-2-enamine in an analogous manner to that described in Example 3 δ (CDCl₃), 2.45

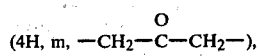
(4H, m, —CH₂—C—CH₂—), 4.30 (2H, m, 1-H, 5-H), 4.50 and 4.55 (total 2H, both s, —CH₂Ph from each isomer), 7.32 (5H, bs, —Ph).

EXAMPLE 5

2-(3-Hydroxyoctyl)-cis-2,4-diazabicyclo[3.3.0]octane-3,7-dione 2-(3-Benzyloxyoctyl)-cis-2,4-diazabicyclo[3.3.0]octane-3,7-dione (5.0 g) and 5% palladium on charcoal (1.5 g) in absolute ethanol (100 ml) were hydrogenated at room temperature and one atmosphere for 2 hours. The suspension was filtered through a pad of Celite and the residue washed with chloroform and the combined organic phases concentrated in vacuo. The residual gum was purified by column chromatography (silica gel; eluted with 12% methanol, 58% ether 30% dichloromethane) giving two diastereomeric products:
Less Polar Isomer, m.p. 55°–6° (from ether/n-hexane)
More Polar Isomer, m.p. 83°–4° (from ether/n-hexane/chloroform)

EXAMPLE 6

2-(3-Cyclohexyl-3-hydroxypropyl)-cis-2,4-diazabicyclo[3.3.0]octane-3,7-dione

The title compound was obtained as a mixture of diastereomers in an analogous manner to that described in Example 5. The material obtained was used for subsequent reactions without separation into the two component isomers.

EXAMPLE 7

2-(3-Acetoxyoctyl)-cis-2,4-diazabicyclo/3.3.0/octane-3,7-dione 2-(3-Hydroxyoctyl-cis-2,4-diazabicyclo[3.3.0]octane-3,7-dione (1.61 g) (more polar isomer) was dissolved in pyridine (6.0 ml) and acetic anhydride (6.0 ml) and set aside at room temperature for 18 hours. The solution was diluted with chloroform and washed with water, N hydrochloric acid, aqueous sodium bicarbonate solution, then finally water, then dried (MgSO₄) and the solvent removed in vacuo. The residual glass was recrystallized from chloroform/ether to give 2-(3-acetoxyoctyl)-cis-2,4-diazabicyclo[3.3.0]octane-3,7-dione as colourless needles m.p. 85°–6° (Rf 0.50, silica 6:3:1 ether:dichloromethane:methanol).

The acetate of the less polar alcohol was prepared in a similar manner, m.p. 92°–3° (Rf 0.45, silica, 6:3:1:ether:dichloromethane:methanol).

EXAMPLE 8

2-(3-Acetoxy-3-cyclohexylpropyl)-cis-2,4-diazabicyclo[3.3.0]octane-3,7-dione

The title compound was obtained as a mixture of diastereomers in an analogous manner to that described in Example 7.

EXAMPLE 9

1β,5β,7α-2-(3-Acetoxyoctyl)-7-hydroxy-2,4-diazabicyclo[3.3.0]octan-3-one 2-(3-Acetoxyoctyl)-cis-2,4-diazabicyclo[3.3.0]octane-3,7-dione (400 mg) (Isomer of m.p. 85°–6°) in ethanol (16 ml) was treated at +5° with sodium borohydride (52 mg) with stirring. After 4 hours at room temperature, excess ethanol was removed in vacuo and the residue diluted with water and the product extracted into ether. The extract was dried (MgSO₄), the solvent removed in vacuo, and the residue recrystallized from ether/hexane giving 1β,5β,7α-2-(3-acetoxyoctyl)-7-hydroxy-2,4-diazabicyclo[3.3.0]octan-3-one as colourless crystals, m.p. 63°–4°.

The isomer of m.p. 92°–3° was similarly reduced giving colourless needles of m.p. 74°–5°.

EXAMPLE 10

1β,5β,7α-2-(3-Acetoxy-3-cyclohexylpropyl)-7-hydroxy-2,4-diazabicyclo[3.3.0]octan-3-one The title compound was obtained as a mixture of diastereomers in an analogous manner to that described in Example 9.

EXAMPLE 11

1β,5β,7α-2-(3-Acetoxyoctyl)-7-(4-methylphenylsulphonyloxy)-2,4-diazabicylo-[3.3.0]octan-3-one 1β,5β,7α-2-(3-Acetoxyoctyl)-7-hydroxy-2,4-diazabicyclo[3.3.0]octan-3-one (312 m) (Isomer of m.p. 63°–4°) in dry pyridine (2.4 ml) was treated at room temperature with p-toluenesulphonyl chloride (240 mg). The orange solution was set aside at room temperature for 24 hr then diluted with chloroform and washed with excess 2 N hydrochloric acid. The organic extract was dried (MgSO₄) and the solvent removed in vacuo and the residual gum purified by column chromatography (silica, elution with 23:2 ether:methanol) giving 1β,5β,7α-2-(3-acetoxyoctyl)-7-(4-methylphenylsulphonyloxy)-2,4-diazabicyclo/3.3.0/octan-3-one as colourless crystals, m.p. 59°–60° (from ether:hexane).

The isomer of m.p. 74°–5° was similarly converted into the p-toluenesulphonate as colourless plates, m.p. 51°–2° (from ether:hexane).

EXAMPLE 12

1β,5β,7α-2-(3-Acetoxy-3-cyclohexylpropyl)-7-(4-methylphenylsulphonyloxy)-2,4-diazabicyclo[3.3.0]octan-3-one The title compound was obtained as a mixture of diastereomers in an analogous manner to that described in Example 11.

EXAMPLE 13

1β,5β,7α-2-(3-Acetoxyoctyl)-7-(3-methoxycarbonylpropylthio)-2,4-diazabicyclo[3.3.0]octan-3-one -Thiobutyrolactone (510 mg) was dissolved in methanolic sodium methoxide [from sodium (120 mg and dry methanol (10.0 ml)] and set aside at room temperature for 2 hours. The solvent was removed in vacuo and the residue dissolved in dry dimethyl-sulphoxide (10.0 ml). 1β,5β,7α-2-(3-Acetoxyoctyl)-7-(4-methylphenylsulphonyloxy)-2,4-diazabicyclo[3.3.0]octan-3-one (1.20 g) (isomer of m.p. 59°–60°) in dimethylsulphoxide (4.0 ml) was added in one portion to the thiolate solution (6.2 ml) prepared above and the mixture set aside at room temperature for 18 hours. The solution was then diluted with 0.5% aqueous sodium dihydrogen phosphate solution (150 ml) and the product extracted into ethyl acetate. The extract was washed with water, dried (MgSO$_4$), the solvent removed in vacuo and the product purified by column chromatography (silica, elution with 3:100 methanol:ether) giving 1β,5β,7α-2-(3-Acetoxyoctyl)-7-(3-methoxycarbonylpropylthio)-2,4-diazabicyclo[3.3.0]octan-3-one as a colourless glass, (CDCl$_3$) 0.87 (3H, bt, —CH$_2$—CH$_3$), 2.04 (3H, s, —C—CH$_3$), 2.3 (2H, m, —CH$_2$—CO$_2$Me), 2.5 (2H, m, —CH$_2$—S—), 3.67 (3H, s, —O—CH$_3$), 4.25 (2H, m, 1-H, 5-H) (Rf 0.50, silica, 1:20 methanol:ether). From 1β,5β,7α-2-(3-acetoxyoctyl)-7-(3-methylphenylsulphonyloxy)-2,4-diazabicyclo[3.3.0]octan-3-one of m.p. 74°–5° was similarly obtained the other isomer, δ (CDCl$_3$) 0.86 (3H, bt, —CH$_2$CH$_3$), 2.03 (3H, s, —CO—CH$_3$), 2.3 (2H, m, —CH$_2$CO$_2$Me), 2.5 (2H, m, —CH$_2$—S—), 3.66 (3H, s, —O—CH$_3$) and 4.19 (2H, m, 1-H, 5-H). (Rf 0.40, silica, 1:20 methanol ether).

EXAMPLE 14

1β,5β,7α-2-(Acetoxy-3-cyclohexyl)propyl-7-(3-methoxy-carbonylpropylthio-2,4-diazabicyclo[3.3.0]octan-3-one The title compound was obtained as a mixture of diastereomers in an analogous manner to that described in Example 13.

EXAMPLE 15

1β,5β,7α-7-(3-carboxypropylthio)-2-(3-hydroxyoctyl)-2,4-diazabicycloz[3.3.0]-octan-3-one 1β,5β,7α-2-(3-Acetoxyoctyl)-7-(3-methoxycarbonylpropythio)-2,4-diazabicyclo[3.3.0]octan-3-one (830 mg) (Isomer of Rf 0.40, silica, 1:20 methanol:ether) in methanol (8.5 ml) was treated with 2 N aqueous sodium hydroxide (5.2. ml) and set aside at room temperature for 1.5 hours. The solution was diluted with water, washed with ether, and the aqueous phase acidified to pH 3 with dilute hydrochloric acid. The product was extracted into chloroform, the extract dried (MgSO$_4$), the solvent removed in vacuo and the residue recrystallized from chloroform:ether giving the more polar isomer of 1β,5β,7α-7-(3-carboxypropylthio)-2-(3-hydroxyoctyl)-2,4-diazabicyclo[3.3.0]octan-3-one as colourless prisms, m.p. 74°–5° (Compound No. 1).

From the ester of Rf 0.50 (silica, 1:20 methanol:ether) was similarly obtained the less polar isomer of 1β,5β,7α-7-(3-carboxypropylthio)-2-(3-hydroxyoctyl)-2,4-diazabicyclo[3.3.0]octan-3-one as colourless prisms, m.p. 79°–80° (Compound No. 2).

EXAMPLE 16

1β,5β,7α-7-(3-Carboxypropylthio)-2-(3-hydroxy-3-cyclohexylpropyl)-2,4-diazabicyclo[3.3.0]octan-3-one The title compound was obtained as a mixture of diastereomers in an analogous manner to that described in Example 15.

The isomers were separated by preparative T.L.C. giving:

Less Polar Isomer, as colourless crystals, m.p. 148°–149.5° δ (CDCl$_3$) 2.46 (2H, m, —CH$_2$CO$_2$H), 2.64 (2H, m, —CH$_2$—S—), 3.3 (1H, m, CH—O—), 4.18 (2H, m, 1-H, 5-H), 6.1 (3H, b OH, —NH —CO$_2$H). (Compound No. 3).

More Polar Isomer, as a colourless glass, δ (CDCl$_3$) 2.4 (2H, m, —CH$_2$—CO$_2$H), 2.6 (2H, m, —CH$_2$—S—), 3.3 (1H, m, —CH—OH), 4.2 (2H, m, 1-H, 5-H); m/e 384 (C$_{19}$H$_{32}$N$_2$O$_4$S requires m/e 384) (Compound No. 4).

The following Examples illustrate pharmaceutical compositions according to the present invention wherein the "active ingredient" is a compound of formula (I) as defined above, e.g. especially 1β,5β,7α-2-(3-cyclohexyl-3α-hydroxypropyl)-7-(3-carboxypropylthio)-2,4-diazabicyclo[3.3.0]octan-3-one.

EXAMPLE A

| Tablet | In one tablet |
| --- | --- |
| Active ingredient | 5.0 mg |
| Lactose B.P. | 82.0 mg |
| Starch B.P. | 10.0 mg |
| Povidone B.P.C. (polyvinylpyrrolidone | 2.0 mg |
| Magnesium Stearate | 1.0 mg |

Mix together the active ingredient, lactose and starch. Granulate the powders using a solution of the povidone in Purified Water. Dry the granules, and the Magnesium Stearate and compress to produce tablets, 100 mg per tablet.

EXAMPLE B

| Capsule | In one capsule |
| --- | --- |
| Active ingredient | 10 mg |
| Lactose | 79 mg |
| Starch | 10 mg |
| Magnesium Stearate | 1 mg |

Mix the powders in a powder blender, fill into hard gelatin capsules, 100 mg per capsule.

EXAMPLE C

| 1 μg/ml Injection | |
| --- | --- |
| Active ingredient | 100 μg |
| Water for Injection | to 100 ml |

Dissolve the active ingredient in the Water for Injection. Sterilise the solution by filtration through a membrane filter, 0.22 um pore size, collecting the filtrate in a sterile receiver. Under aseptic conditions, fill the solution into sterile glass ampoules, 1 ml per ampoule. Seal by fusion of the glass.

EXAMPLE D

| 10 µg/ml Injection | |
|---|---|
| Active ingredient | 1 mg |
| Ethyl Alcohol | 10 ml |
| Propylene Glycol | 30 ml |
| Water for Injection | to 100 ml |

Dissolve the active ingredient in the Ethyl Alcohol, add the Propylene Glycol and dilute to volume with Water for Injection.

Sterilise the solution by filtrate through a membrane filter, 0.22 µm pore size, collecting the filtrate in a sterile vessel. Under aspetic conditions, fill the solution into sterile glass vials, 10 ml per vial. Close with a sterile rubber plug and secure with an aluminium collar.

BIOLOGICAL ACTIVITY

Cardiovascular effects in rats

Male normotensive rats Wistar (Charles River) strain, (250-350 g) were anesthetised (chloroform) prior to cannulation of the left femoral vein and anaesthesia maintained by intravenous chloralose (60 mg/kg). Pulsatile blood pressure was recorded from the left femoral artery with an electronic transducer (Bell and Howell Type 4-327 L221) and integrated heart rate was measured with a cardiotachometer triggered from the arterial pressure waves.

The test compound was administered as a solution in physiological saline by intravenous injection via the femoral cannula. The responses recorded were allowed to return to the preinjection levels between successive administrations.

Injections of the vehical alone in volumes equivalent to those containing drug did not produce hypotension.

Compounds Nos. 1, 2, 3 and 4 were each found to have a hypotensive effect of less than 0.001-times that of prostacyclin as a standard.

Inhibition of Platelet Aggregation

Aggregation of platelets in 1 ml. of fresh human platelet rich plasma (PRP) was monitored in a Born aggregometer.

The compound to be tested was added to the PRP, and the resulting mixture incubated at 37° C. for 1 minute after which platelet aggregation was stimulated by the addition of adenosine diphosphate (ADP) to a concentration of 5 uM.

The anti-aggregatory effect of the compound was assessed by measuring the percentage inhibition of platelet aggregation in the presence of the compound as compared when it was completely absent.

The following relative potencies were found with respect to PGE$_1$ as a standard: Compound No. 1, 0.06x; Compound No. 3, 9x and 10.5x; Compound No. 4; 0.05x.

Anti-ulcer Activity

Compounds Nos. 1 and 3 were found to have respectively 0.50 and 0.65-times the potency of PGE$_2$ for the reduction of indomethacin-induced gastric ulceration in the rat.

We claim:

1. A compound of the formula

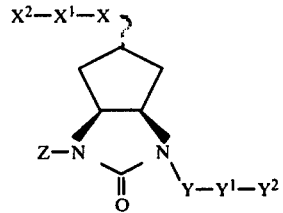

wherein

X represents a sulphur atom (—S—) or oxygen atom (—O—) in the α or β-configuration;

X$^1$ represents a C$_{1-5}$ straight chain or branched alkylene group or C$_{3-5}$ straight chain or branched alkenylene group;

Z represents a hydrogen atom or a C$_{1-4}$ straight chain or branched alkyl group;

Y represents a group of formula —CR$_2$—CH$_2$— in which each R is independently selected from hydrogen and methyl;

Y$^1$ represents a methylene group substituted by hydroxyl, a methylene group substituted by hydroxyl and C$_{1-6}$ alkyl, a methylene group or a carbonyl group; and Y$^2$ represents a C$_{1-7}$ straight chain or branched alkyl group, phenyl, benzyl or a C$_{4-7}$ cycloalkyl;

X$^2$ represents a carboxyl, carboxamide, hydroxymethylene, C$_{1-6}$ alkoxycarbonyl or 5-tetrazolyl group; or a salt of said compound of formula (1) when either X$^2$ is carboxyl, or Z is hydrogen or when X$^2$ is carboxyl and Z is hydrogen.

2. A compound as claimed in claim 1 wherein X represents a sulphur atom in the α-configuration.

3. A compound as claimed in claim 1 or claim 2 wherein X$^2$ represents a carboxyl group.

4. A compound as claimed in claim 1 or 2 wherein Z represents a hydrogen atom.

5. A compound as claimed in claims 1 or 2 wherein Y$^1$ represents a methylene group substituted by hydroxyl in the β-configuration.

6. 1β, 5β, 7α-2-(3-Cyclohexyl-3-β-hydroxypropyl)-7-(3-carboxypropylthio)-2,4-diazabicyclo[3.3.0.]octan-3-one, of formula

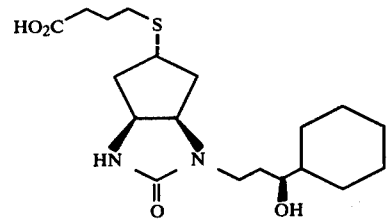

7. An antithrombotic composition comprising an effective antithrombotic amount of a compound of claim 1 or a pharmaceutically acceptable salt thereof when either X$^2$ is carboxyl or Z is hydrogen, or X$^2$ is carboxyl and and Z is hydrogen, together with at least one pharmaceutical carrier or excipient.

8. The composition of claim 7 in which the active ingredient is 1β,5β,7α-2-(3-cyclohexyl-3-β-hydroxypropyl)-7-(3-carboxypropylthio)-2,4-diazabicyclo octan-3-one.

9. A method for the treatment or prophylaxis of a thrombo-embolic disorder in a mammal which comprises administering to the said mammal a compound of claim 1 or a pharmaceutically acceptable salt thereof in an effective amount to treat or prevent said disorder.

10. A method of reducing or preventing the undesired aggregation of blood platelets in a mammal which comprises administering to said mammal a compound of claim 1 or a pharmaceutically acceptable salt thereof in an effective amount to reduce or prevent the undesired aggregation of blood platelets.

11. The method of claim 9 in which the the compound is 1β,6β, 7α(-2-(3-cyclohexyl-3-β-hydroxypropyl)-7-(3-carboxypropylthio)-2,4-diazabicyclo[3.3.0]octan-3-one.

12. The method of claim 10 in which the compound is 1β,5β, 7α-2-(3-cyclohexyl-3-β-hydroxypropyl)-7-(3-carboxypropylthio)-2,4-diazabicyclo[3.3.0]octan-3-one.

* * * * *